(12) United States Patent
Golabek, Jr. et al.

(10) Patent No.: US 7,445,152 B2
(45) Date of Patent: Nov. 4, 2008

(54) LABEL SYSTEM AND METHOD FOR LABEL ALIGNMENT AND PLACEMENT

(75) Inventors: Robert S. Golabek, Jr., Towaco, NJ (US); Cathy Shea, Upper Saddle River, NJ (US); Kirk D. Swenson, North Caldwell, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 691 days.

(21) Appl. No.: 11/124,007

(22) Filed: May 6, 2005

(65) Prior Publication Data

US 2006/0249582 A1   Nov. 9, 2006

(51) Int. Cl.
    *G06K 7/10*   (2006.01)
(52) U.S. Cl. .................................. 235/462.01
(58) Field of Classification Search .............. 235/462.01
    See application file for complete search history.

(56) References Cited

U.S. PATENT DOCUMENTS 5,663,545 A   9/1997   Marquiss et al.

2002/0093189 A1   7/2002   Krupa

FOREIGN PATENT DOCUMENTS

| EP | 0979777 | 2/2000 |
|----|---------|--------|
| EP | 979777 A | 2/2000 |
| EP | 1224977 A1 | 7/2002 |

OTHER PUBLICATIONS

PCTUS2006016978-International Search Report.

*Primary Examiner*—Karl D. Frech
*Assistant Examiner*—Tae W Kim
(74) *Attorney, Agent, or Firm*—Mark J. Schildkraut

(57) ABSTRACT

The present invention is a label system and method for label alignment and placement on a container. The label system includes a first label or a container whereby the first label includes alignment symbology and a second label having an alignment area corresponding to the alignment symbology of the first label. The second label is positioned on the container whereby the alignment area of the second label is aligned with the alignment symbology of the first label. Visibility enhancement indicia may be provided adjacent the alignment area to increase the visibility of the alignment area to the user. Other indicia may be used to align the container in a holder for bar code scanning.

20 Claims, 11 Drawing Sheets

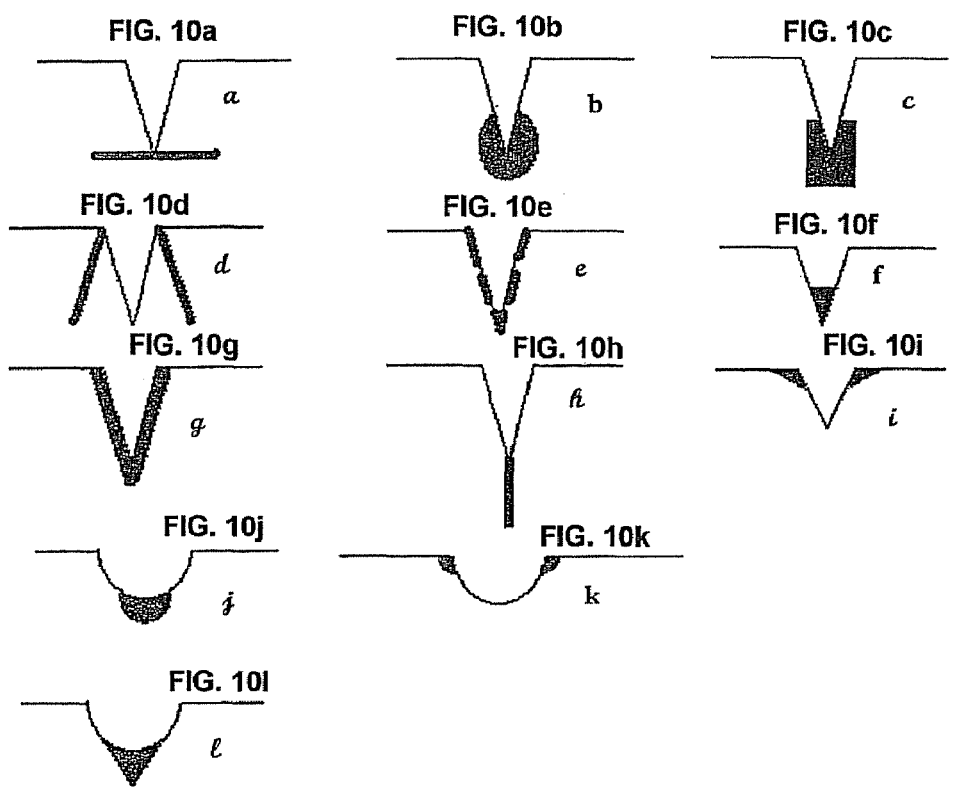

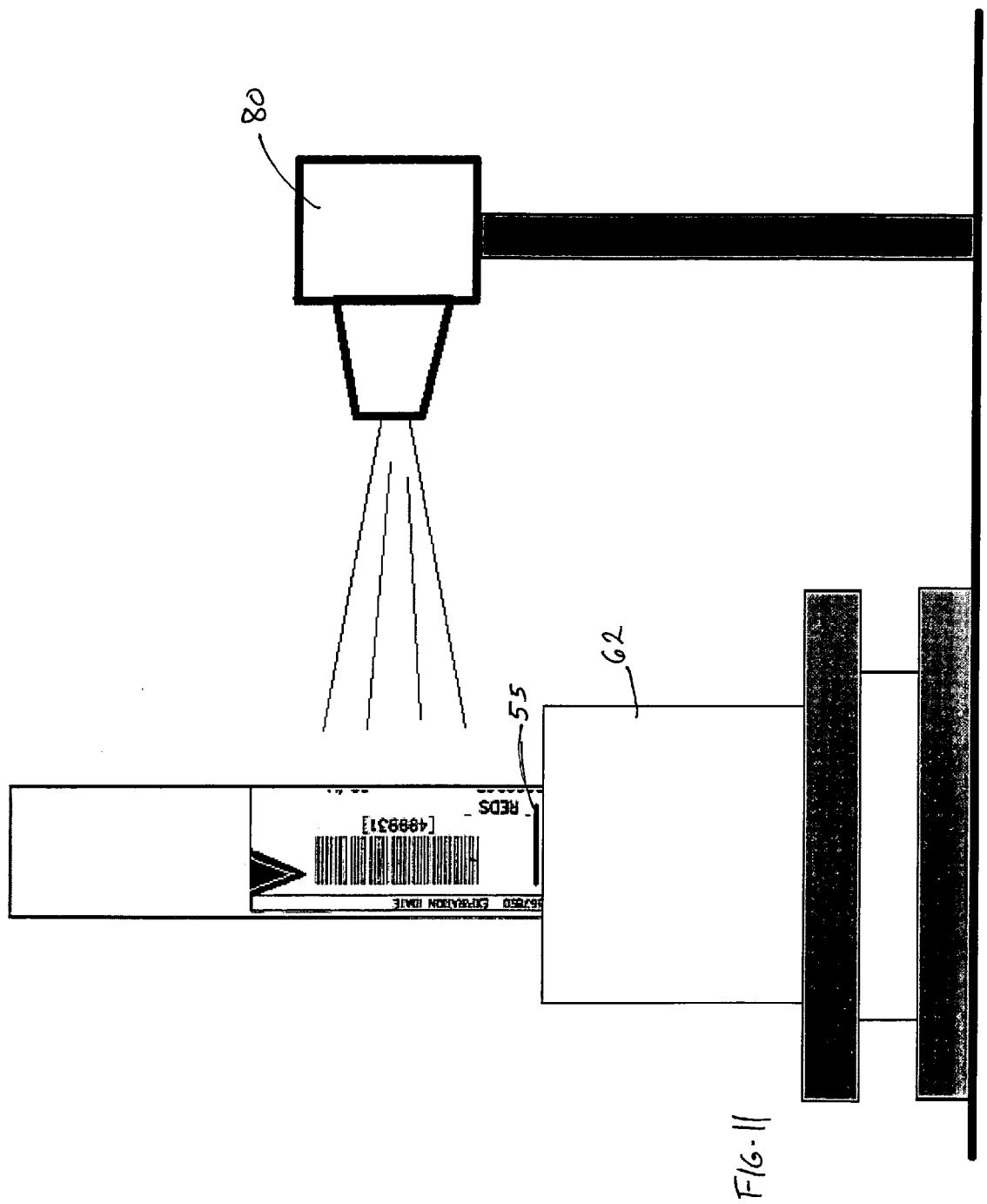

LABEL SYSTEM AND METHOD FOR LABEL ALIGNMENT AND PLACEMENT

BACKGROUND OF THE INVENTION

1. Field of the Invention

The present invention relates to a label, label system and method, and more particularly to positioning of such label when affixed to a container.

2. Description of Related Art

Proper placement of a printed label on a container is, at times, important for ensuring subsequent reading of the information printed on the label. If not properly placed, the printed information may not be easily seen, or cannot easily be scanned, by automated equipment.

Proper placement of the bar code information on a specimen collection container is often important to ensure proper scanning of the encoded information by various clinical equipment and analytical testing instrumentation. If the bar code information is not properly positioned on the sample container, the scanner of the instrumentation may not be able to read the bar code, thus requiring the operator to manually scan the bar code information, or manually enter the bar code information into the instrumentation.

SUMMARY OF THE INVENTION

Accordingly, a need exists for a system and method which is capable of properly aligning a label on a specimen collection container. Further, a need exists for a system and method capable of printing indicia on a label, such as bar code information, in a standard position with respect to the container for subsequent automated reading or scanning. It should be noted that the term "indicia" is meant to incorporate singular or a plurality indication information.

In accordance with an embodiment of the present invention, a label system and method are provided for proper alignment and placement of a label on a container. Desirably, a label is provided that is capable of being affixed to a container having alignment symbology thereon. The label includes an alignment area corresponding to the alignment symbology of the container and at least one visual enhancement indicia adjacent to at least a portion of the alignment area. In one embodiment, the visual enhancement indicia has a width that is less than the label width. In another embodiment the visual enhancement indicia identifies at least one characteristic of the container.

In another embodiment of the invention, a set of labels for labeling containers having alignment symbology thereon is provided. The set includes a plurality of labels having an alignment area for corresponding to the alignment symbology of the container, and visual enhancement indicia adjacent to at least a portion of the alignment area. The labels are affixed to a surface, prior to labeling the containers with the labels.

In yet another embodiment of the invention, a label is provided that is capable of being affixed to a container having alignment symbology thereon. The label includes machine readable information on the label and demarcation indicia on the label to assist with aligning the container for reading by the machine.

DESCRIPTION OF THE DRAWINGS

FIGS. 10a, 10b, 10c, 10d, 10e, 10f, 10g, 10h, 10i, 10j, 10k, 10l each illustrate variants of the visibility enhancement indicia, in accordance with an embodiment of the present invention; and FIG. 11 illustrates a container bearing a second label having demarcation indicia, the container and label being positioned in a holder, in accordance with an embodiment of the present invention.

DETAILED DESCRIPTION

Figure 1:
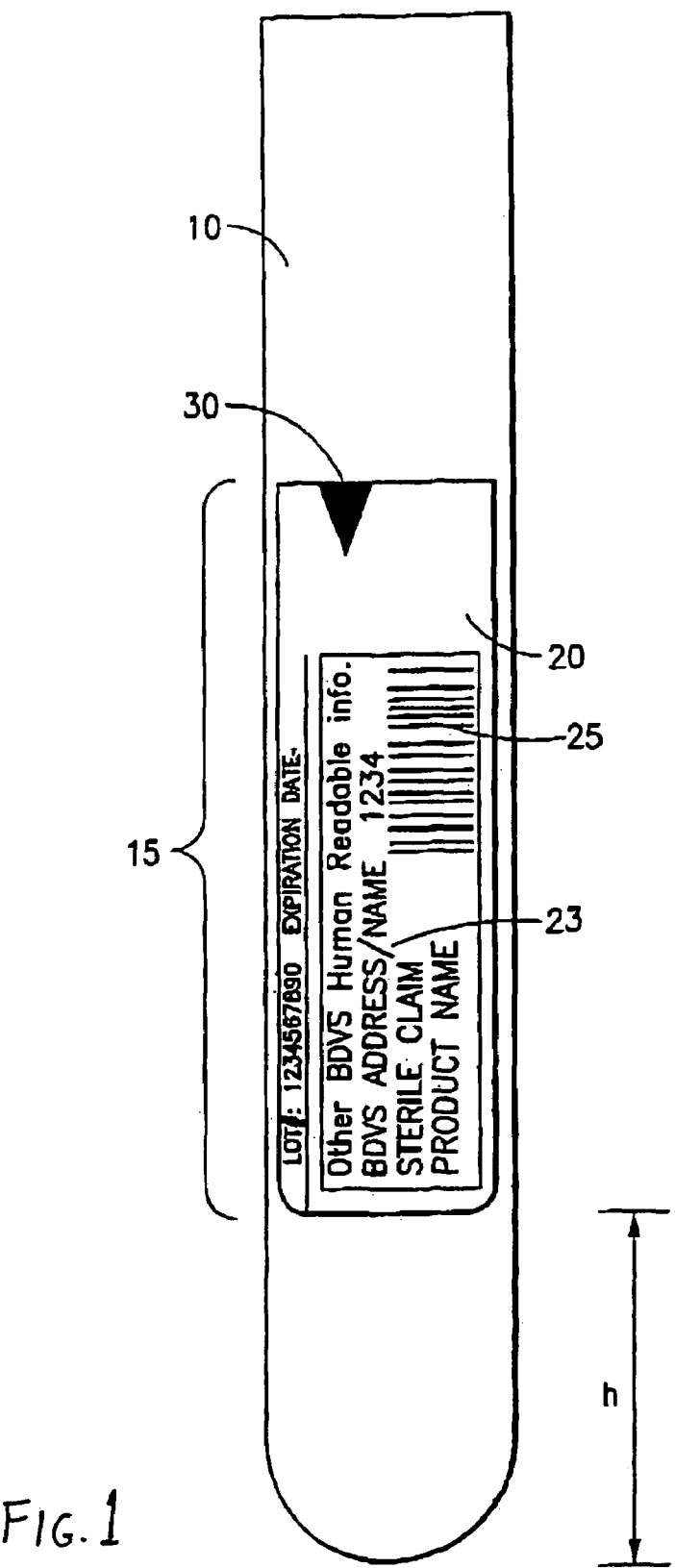
FIG. 1 illustrates a specimen container including a first label having alignment symbology and container identification symbology.

Referring to the drawings in which like reference characters prefer to like parts throughout the several views thereof, FIG. 1 illustrates a container 10 with an alignment symbology 30 appearing on an outer surface of container 10. Alignment symbology 30 is designed to aid in the alignment of an identification label subsequently placed over the container. The alignment symbology may be any type of symbol capable of assisting in the proper positioning and alignment of a subsequently placed label. For example, the alignment symbology may be a distinct shape in the form of a graphic or pictorial representation, such as a triangle, rectangle, diamond, circle, or the like, and combinations thereof. Alternatively, the alignment symbology may be a protrusion which can be felt with the finger.

As shown in FIG. 1, container 10 includes a first label 20 (sometimes referred to as a pre-label) affixed to the outer surface of the container or label bearing area 15, with alignment symbology 30 printed on label 20. Label 20 may further contain additional encoded or printed information thereon such as container identification symbology. Such identification symbology includes a bar code 25 and/or an alphanumeric indicia 23, either or both of which may include information identifying the specific type of the container, the manufacturer lot number, the expiration date, the size and/or shape of the container and the reagents and/or additives included within the container.

Figure 2:
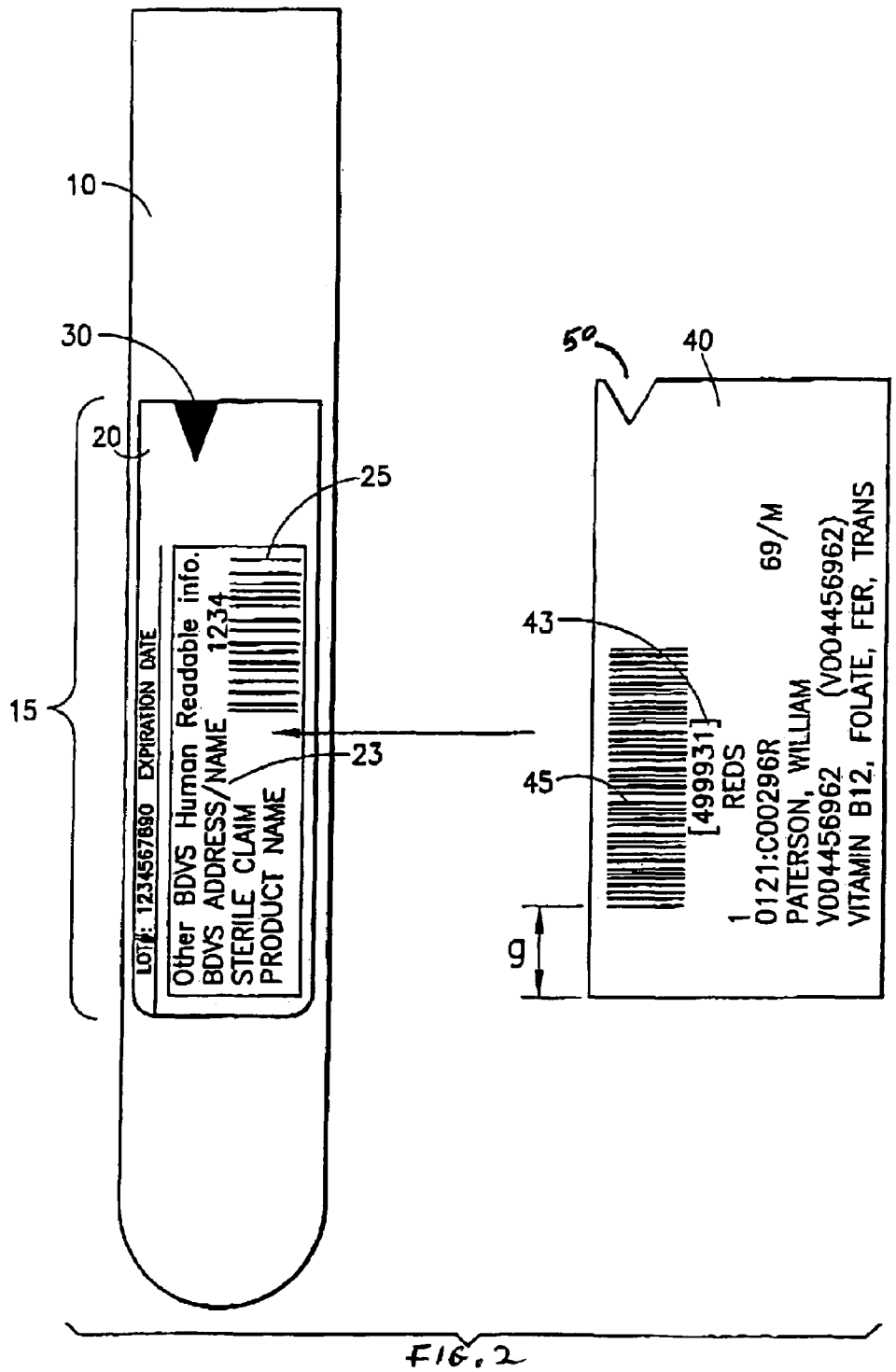
FIG. 2 illustrates a second label including an opening corresponding to the alignment symbology of first label of the specimen container of FIG. 1.

As shown in FIG. 2, an identification label 40 (sometimes referred to as an over-label) is provided for placement on container 10. Identification label 40 may include encoded or printed information thereon, such as a bar code 45 and/or an alphanumeric indicia 43, either or both or which may represent an identification of the sample contained within the container, information identifying the patient, what analyses are to be conducted on the sample and sampling information such as date and time of sampling. Identification label 40 may be generated by a printer located at a nursing station or in a centralized laboratory or printed at the bedside with a portable printer.

Figure 4:
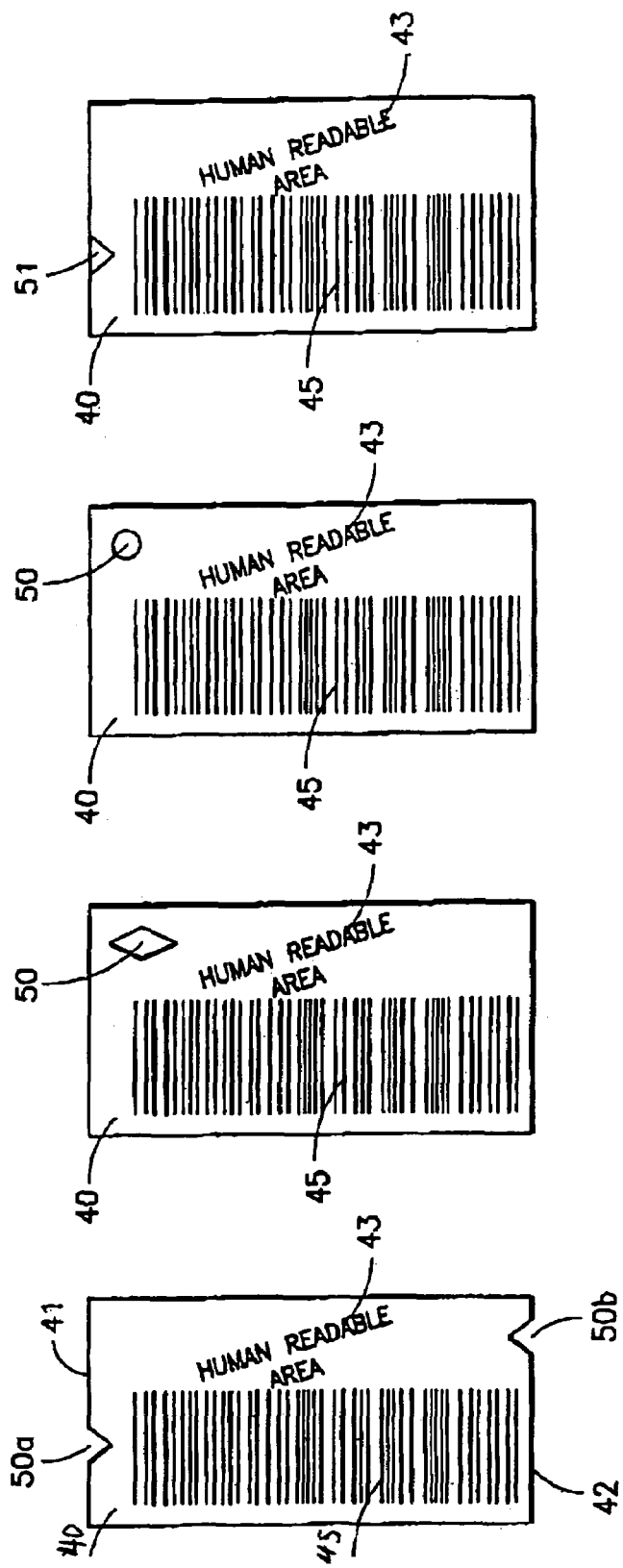
FIGS. 4a, 4b, 4c and 4d illustrate alternative embodiments of the label of the present invention whereby both first container label and second label must align to ensure proper placement.

Identification label 40 is provided as a second label capable of being affixed over label 20. Identification label 40 includes an alignment area 50 corresponding to alignment symbology 30 of label 20. Alignment area 50 may be an opening or notched cut-away of label 40. For example, as shown in FIG. 2, alignment symbology 30 is in the form of a v-shaped triangle and alignment area 50 is a v-shaped notch appearing on the edge of label 40. Alternatively, alignment area 50 may be a transparent portion having a shape designed to fit over alignment symbology 30, such as transparent portion 51 as shown in FIG. 4*d*.

Figure 3:
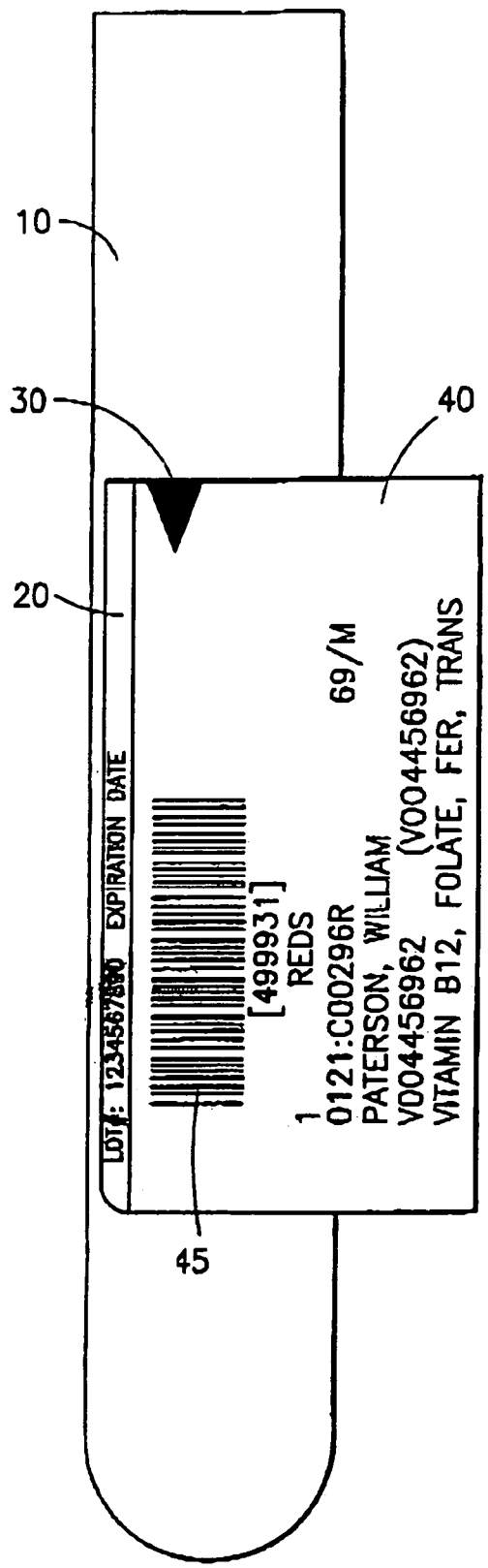
FIG. 3 illustrates a specimen container as in FIGS. 1 and 2 including the second label of FIG. 2 properly aligned on the container.

As shown in FIG. 3, identification label 40 is positioned on container 10 such that alignment area 50 of identification label 40 is aligned with alignment symbology 30 of label 20, with alignment symbology 30 being detectable through alignment area 50, thereby assuring proper alignment of the identification label on container 10.

It is within the purview of the present invention that alignment symbology 30 and identification label 40 are contrasting colors, for example, alignment symbology 30 is printed in black ink as a geometric shape, and identification label 40 is a white label including alignment area 50 therethrough. Therefore, the sharp contrast between the colors of the alignment symbology 30 and alignment area 50 provides accurate assurance that identification label 40 is properly aligned over container 10.

It is also within the purview of the present invention that alignment symbology 30 includes a protrusion, such as a v-shaped bump and alignment area 50 of identification label 40 is in the form of a v-shaped notch extending through identification label 40. Therefore, the v-shaped notch is aligned with the v-shaped bump of container 10 or container label 20 when identification label 40 is positioned over container label 20, with the v-shape ensuring both vertical and horizontal alignment of identification label 40 on container label 20. Moreover, such a protrusion provides a means for detecting proper alignment both visually and through touch to assure proper placement of identification label 40 over container label 20.

As shown in FIG. 4*a*, container label 20 may include a plurality of alignment areas. Areas 50*a* and 50*b* at opposed label edges 41 and 42. Alignment areas 50*a* and 50*b* are designed to cooperate with two separate alignment symbologies appearing on container 10 and/or container label 20.

It is within the purview of the present invention that alignment symbology 30 can be any shape or form, so long as alignment area 50 of identification label 40 properly corresponds to the shape and/or form of alignment symbology 30.

As shown in FIGS. 4*b*, 4*c*, and 4*d*, alignment area 50 can be in the shape of a diamond, or a circle which shapes would correspond to a similar shape; alignment symbology appearing on container label 20. For ease of use, alignment symbology 30 and alignment area 50 corresponding to shapes which are non-rotationally symmetrical, such as a polygon, to assure proper alignment in both a vertical and horizontal direction and prevent identification label 40 from being improperly skewed or canted.

Figure 8A:
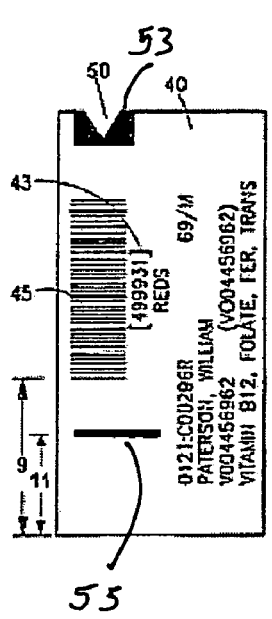
FIGS. 8a, 8b and 8c illustrate second labels according to an embodiment of the present invention having different visibility enhancement indicia.
Figure 8B:
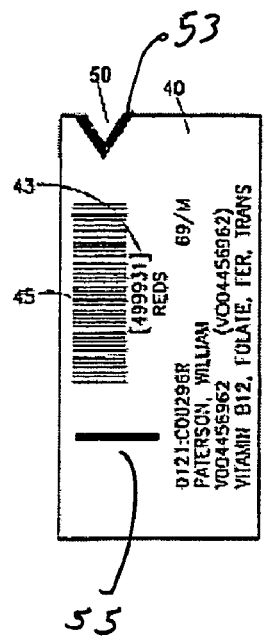
Figure 8C:
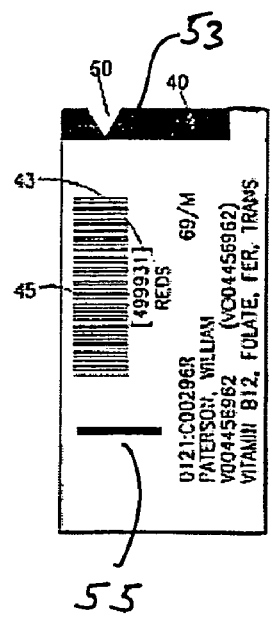

As shown in FIGS. 8*a*, 8*b* and 8*c*, alignment area 50 may be provided with visibility enhancement indicia 53 adjacent the alignment area 50 on the identification label 40. The visibility enhancement indicia 53 may enable, for example, the user to more easily locate the alignment area 50, which may not always easily discernible in the medical practitioner's environment.

In addition, the shape of the visibility enhancement indicia 53 is not particularly limited. For example, if the alignment area is a triangular notch as shown in FIGS. 8*a*, 8*b* and 8*c*, the notch may be bordered by the visibility enhancement indicia, so that the overall pattern is triangular, as shown in FIG. 8*b*, or the notch may be encapsulated in a rectangular shape, so that the overall pattern is rectangular, as in FIG. 8*a*. As shown in FIG. 8*c*, the visibility enhancement indicia 43 may occupy that goes well beyond the immediate area of the alignment area 50. The bar code may be printed using thermal ink-jet printing.

The visibility enhancement indicia may be printed using the same color ink that is used to print the bar code on the identification label, or a different color may be used. When the visibility enhancement indicia is somewhat larger, different colors may be used for the area immediately adjacent the alignment area border and the rest of the visibility enhancement indicia. In addition, the visibility enhancement indicia may be solid, shaded (or some other pattern) or the like.

In accordance with an embodiment of the invention, the characteristics (e.g., shape, color, pattern, etc.) of the visibility enhancement indicia and/or the alignment area may provide additional utility—such as indicating one or more characteristics of the container upon which such indicia is affixed. For example, such indicia may be indicative of one or more substances (or additives) in a biological specimen collection container, the container material (e.g., glass, plastic, plastic type), etc.

Figure 9A:
FIGS. 9a, 9b and 9c illustrate second labels according to an embodiment of the present invention having different visibility enhancement indicia.
Figure 9B:
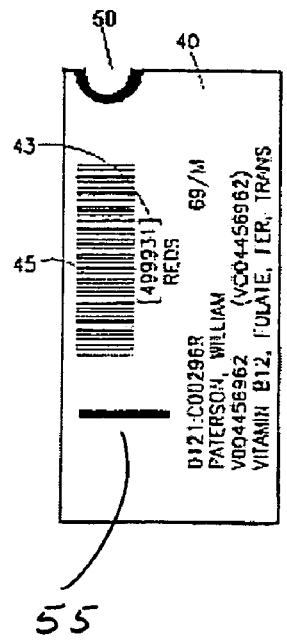
Figure 9C:
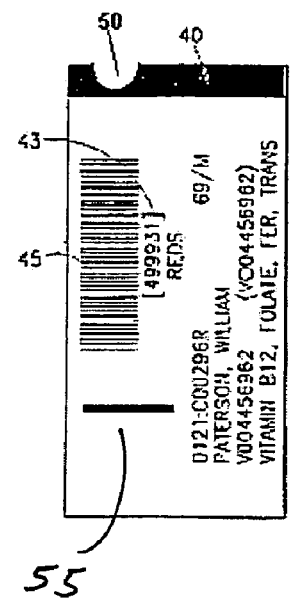

Embodiments in which the alignment notch 50 is semicircular are shown in FIGS. 9*a*, 9*b* and 9*c*, which also show corresponding visibility enhancement indicia. Alternative arrangements for the visibility enhancement indicia are shown in FIGS. 10*a* through 10*l*.

Figure 7:
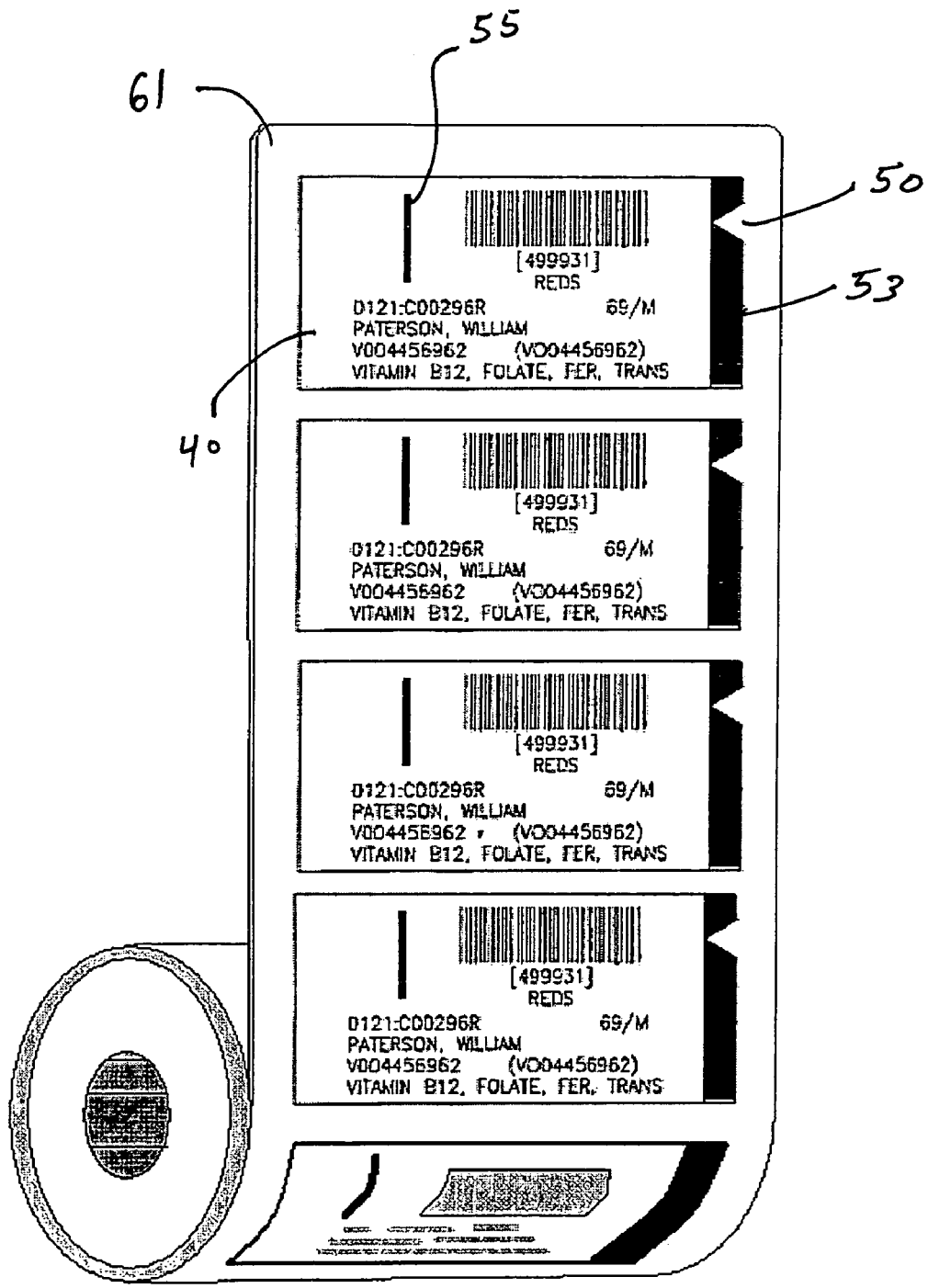
FIG. 7 illustrates a roll of second labels according to an embodiment of the present invention having visibility enhancement indicia adjacent the alignment area border.

As shown in FIG. 7, a plurality of labels 40 having alignment area 50, enhancement indicia 53 and/or demarcation indicia 55 may be printed on a common surface 61. The common surface 61 may be in the form of a roll 70 as shown in FIG. 70, a sheet or some other surface.

Figure 5:
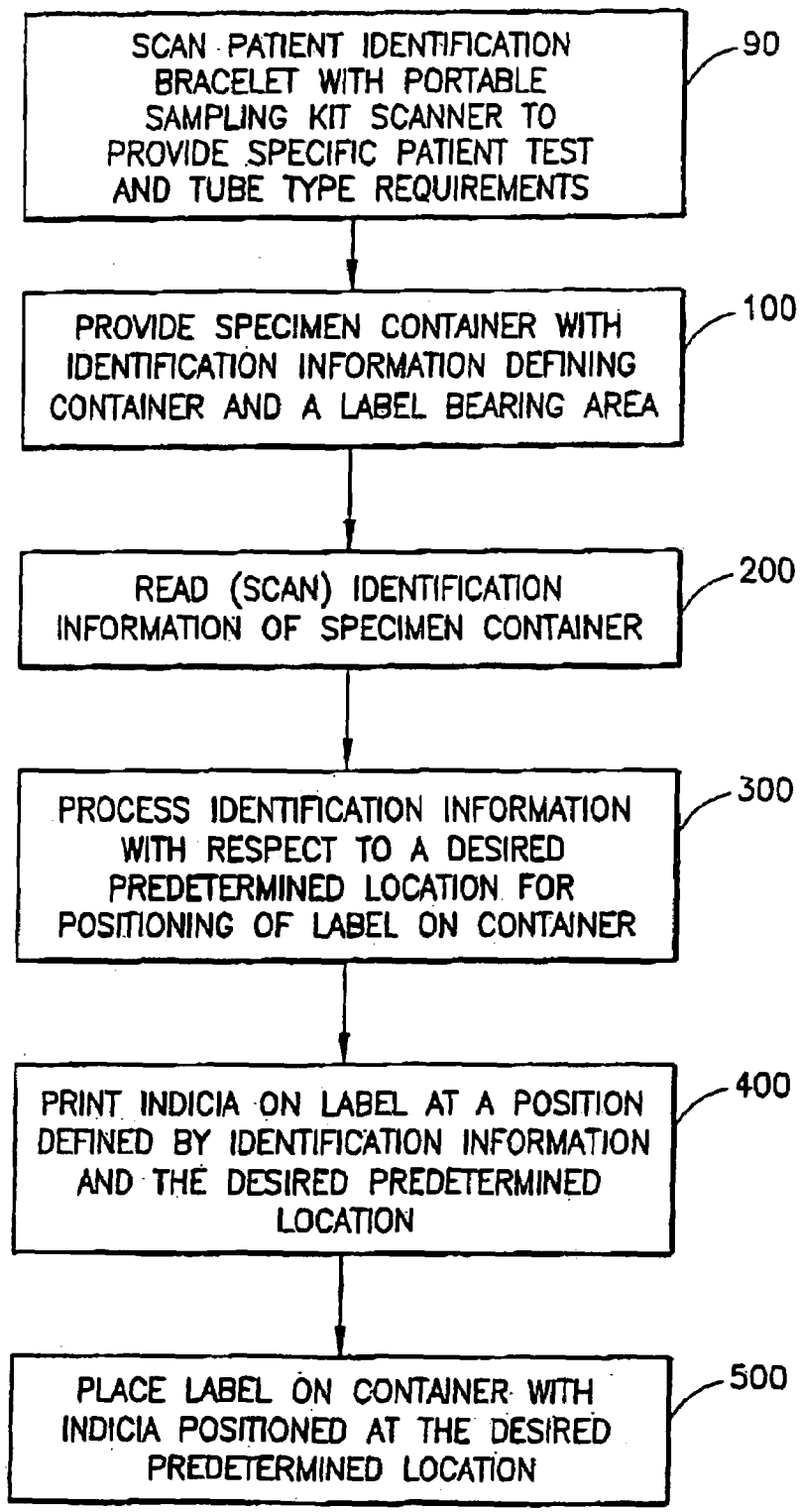
FIG. 5 illustrates a flow chart according to the method for second label generation (printing) and aligned placement of the second label.

The system and method for positionally locating indicia on a label for aligned placement of the indicia at a predetermined position on a container is illustrated in FIG. 5.

The system and method of use begins with an operator, such as a phlebotomist, being provided with a portable sampling kit including a scanner, a microprocessor/display screen and a printer including a supply of labels for printing thereon. As depicted in box 90 of FIG. 5, the patient identification bracelet is scanned with the portable sampling kit scanner to provide specific patient test and associated specific tube type requirements. The phlebotomist then selects the appropriate container 10 for containing the sample requirement. As shown in step 100 in the box diagram of FIG. 3, container 10 in the form of a blood collection tube is provided including bar code 25 including encoded information which identifies the container type and defines the location of label bearing area 15 unique to that container type. The phlebotomist is provided with a listing of patients requiring sampling. Each patient is provided with a patient identification bracelet, preferably including a bar code identification, as is well known in the art. As shown in step 200 of FIG. 5, the phlebotomist then scans bar code 25 on container 10 with the scanner. The portable sampling kit may provide the phlebotomist with confirmation that container 10 is appropriate for containing the sample requiring testing. It is also possible that the phlebotomist does not scan the container until after the collection and prior to requesting the printed label.

Bar code 25 includes encoded information which identifies the container type and defines the location of label bearing area 15 unique to that container type. For example, as depicted in FIG. 1a, container label is positioned at label bearing area 15 of container 10 at a predetermined distance h from the bottom of container 10. This predetermined distance h is determined according to the container type including the size and shape of container 10. The microprocessor of the sampling kit processes the encoded information of bar code 25 identifying the container type with respect to the location of label bearing area 15.

Figure 6:
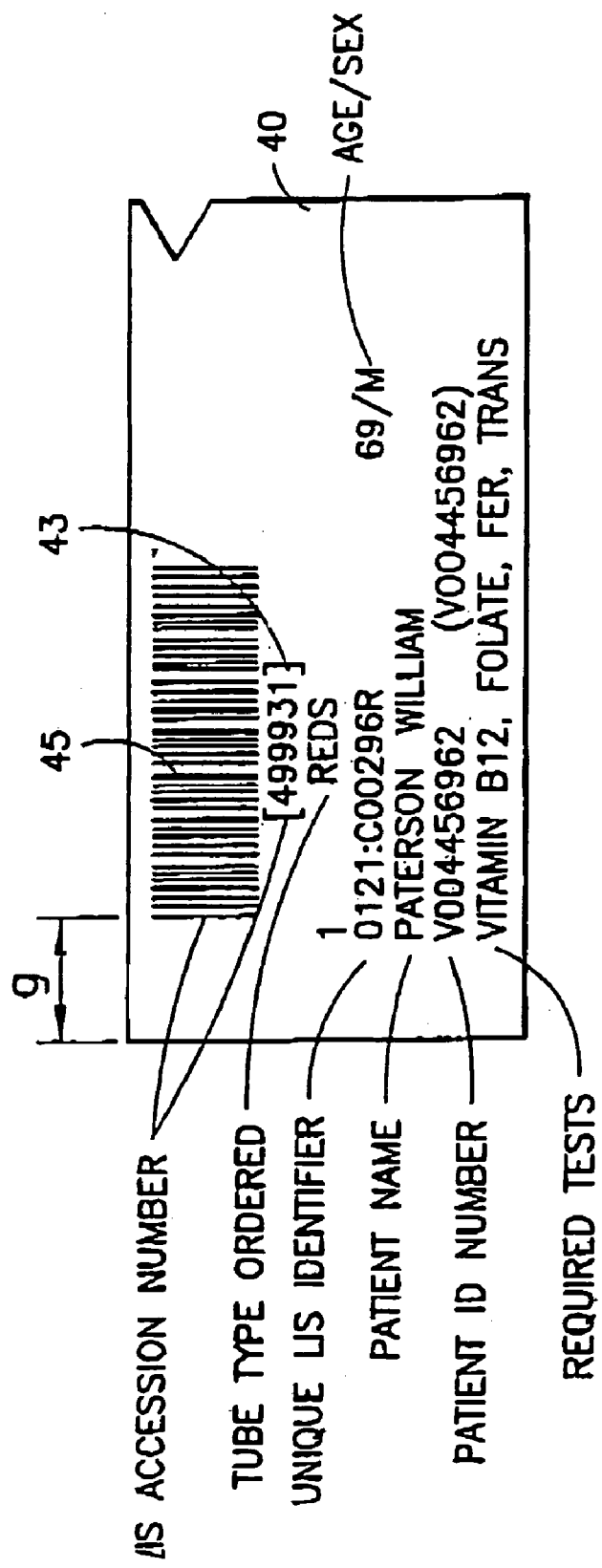
FIG. 6 illustrates the second label of the present invention.

The microprocessor further identifies what information is required for printing on identification label 40 to be affixed to container 10. Identification label 40 is provided with information identifying the patient, the type of sample, and what analyses are to be conducted on the sample, as well as sampling information such as date and time of sampling. As shown in FIG. 6, such information may be encoded as bar code 45, or may be in alphanumeric form, such as alphanumeric indicia 43 or may be provided in both bar code 45 and alphanumeric indicia 43.

After identifying the correctness of the container type and the information to be provided on the label, the microprocessor processes this information to determine the exact location for printing on identification label 40. For example, the microprocessor may be preprogrammed to ensure printing of bar code information at a specific predetermined position on a container, regardless of the size and shape of the container, so as to provide a standard position for such bar code information for all containers to effectuate subsequent reading, for example, by an automated analytical instrument including a bar code scanner. Thus, the microprocessor processes the information previously scanned from container label 20 with respect to the size of identification label 40. The microprocessor then determines the exact location for printing of the identification information on identification label 40 with respect to the predetermined standard position. In all cases, the alignment of the second label 40 onto the container is accomplished by the cut out on the label that is placed onto a matching symbol on the container.

For example, with reference to FIG. 1, the microprocessor processes the scanned information to determine that label bearing area 15 of container 10 is positioned distance h from the bottom of container 10. Further, the microprocessor recognizes from its memory that it is necessary to print bar code 45 on identification label 40 at a predetermined position with respect to label bearing area 15 and container 10, according to a standard position for the specific instrument to conduct the testing. The microprocessor then determines the exact position for printing bar code 45 on identification label 40 according to the desired predetermined position of bar code 45 with respect to label bearing area 15, for example, distance g from a bottom edge of identification label 40. Once the correct tube is identified, the microprocessor then instructs the printer to print the identification information in the form of bar code 45, visibility enhancement indicia 53 and/or demarcation indicia 55 (as described below) on identification label 40 at a position, for example distance g, defined by the predetermined: desired location of bar code 45 with respect to the container information scanned from container label 20, as depicted in step 400 of FIG. 5.

In order to ensure that the content printed on the identification label can be read by a bar code scanner typically attached to an automated sample handling system, the "pucks" or holders that transport the containers must not be permitted to block the scanner. As containers come in different lengths and outside diameters, the pucks typically have an internal biasing mechanism to allow for tubes of different diameters and lengths to maintain a desired position inside the puck without moving. The system of reading the initial bar code, printing a new identification label and placing the identification label over the first label and/or container must not cause the bar code to be obstructed. As shown in FIGS. 9a, 9b and 9c, demarcation indicia 55 may be provided on identification label 40 to ensure proper placement of the bar code with respect to the scanner in the course of operation. As shown in FIG. 1, the demarcation indicia 55 is placed on the identification label so that the user can accurately and reproducibly position the container in the puck 62, ensuring that the bar code can be scanned by, for example, scanner 80.

Different container sizes may require a different location of the demarcation indicia 55 on the identification label 40. This may be accomplished by, for example, providing plural demarcation indicia on the label 40, corresponding to differently sized containers, or by printing a single demarcation indicia 55 dictated by information regarding the type of container on which the label is to be placed. The design of the holder 62 in the FIG. 11 may be, for example, a Bekman Coulter Power Processor carrier. However, the principle of using demarcation indicia may be applied to other instruments and front-end laboratory automation by understanding the bar code reading needs of these instruments and how the bar codes are scanned.

In accordance with an embodiment of the invention, the positioning of demarcation indicia 55 on the second label is defined by information provided on the first label. For example, bar code information 25 of the first label may be used to communicate to a printer positioning information regarding the demarcation indicia.

After bar code-45 is printed on identification label 40, the phlebotomist removes identification label 40 from the printer and affixes it to container 10 at label bearing area 15, according to step 500 of FIG. 5. Container 10 is provided with alignment symbology 30 and identification label 40 is provided with opening 50 corresponding to alignment symbology 30. In this manner, proper alignment and positioning of bar code 45 at a predetermined position with respect to the standard scanning position and the size and shape of container 10 is assured.

Preferably, the alignment indicia are effective so that the bar code label is placed on container so that the bar code is not skewed more than ±7.5 percent with respect to the major axis of the container, pursuant to National Committee for Clinical Laboratory Standards (NCCLS). Preferably, the demarcation indicia are effective so that about 100 percent of the bar codes are able to be read by the scanner.

The foregoing merely illustrates the principles of the invention. It will thus be appreciated that a person skilled in the art will be able to devise numerous arrangements which, although not explicitly shown or described herein, embody the principles of the invention and are thus within its spirit and scope.

For example, although alignment symbology 30 and alignment area 50 are illustrated in the figures toward the top portion of a label, such features may be placed at any portion or portions of a label. In addition, the alignment symbology may be on a label affixed to a container or may be placed on/affixed to the container directly.

What is claimed is:

1. A method for proper alignment of a label on a container comprising:

providing a container having a first label positioned thereon, said first label including alignment symbology;

providing a second label including an alignment area having visibility enhancement indicia adjacent the alignment area, said alignment area of said second label corresponding to said alignment symbology of said first label;

positioning said second label on said container with said alignment area of said second label in alignment with said alignment symbology of said first label such that said alignment symbology is detectable through said alignment area, thereby assuring proper alignment of said second label on said container.

2. The method of claim 1, wherein said alignment area is an opening in said second label.

3. The method of claim 2, wherein said alignment symbology is a protrusion on said first label.

4. The method of claim 1, wherein said alignment area is a transparent portion of said second label.

5. The method of claim 1, further comprising providing the second label with demarcation indicia, positioned to align the container bearing the second label in a holder, so that a bar code on the container can be read by a bar code scanner when the container is in the holder.

6. A method for proper alignment of a label on a container comprising:

providing a container having a first label positioned thereon, said first label including alignment symbology;

providing a second label including an alignment area, said alignment area of said second label corresponding to said alignment symbology of said first label;

positioning said second label on said container with said alignment area of said second label in alignment with said alignment symbology of said first label such that said alignment symbology is detectable through said alignment area, thereby assuring proper alignment of said second label on said container the second label further comprising demarcation indicia, positioned to align the container bearing the second label in a holder, thereby enabling information on the container to be read when the container is in the holder.

7. The method of claim 6, further including the step of providing visibility enhancement indicia adjacent the alignment area on the second label.

8. The method of claim 6, wherein said alignment area is an opening in said second label.

9. The method of claim 6, wherein said alignment symbology is a protrusion on said first label.

10. The method of claim 6, wherein said alignment area is a transparent portion of said second label.

11. A label system for ensuring proper positioning of information on a label, comprising:

a first label comprising alignment symbology; and a second label comprising an alignment area corresponding to said alignment symbology of said first label, and having visibility enhancement indicia adjacent the alignment area;

whereby said second label is positioned over said first label whereby the alignment area of the second label is aligned with the alignment symbology of the first label.

12. The label system of claim 11, wherein said alignment area is an opening in said second label.

13. The label system of claim 11, wherein said alignment symbology is a protrusion on said first label.

14. The label system of claim 11, wherein said alignment area is a transparent portion of said second label.

15. The label system of claim 11, wherein the second label further comprises demarcation indicia, positioned to align the container bearing the second label in a holder, so that information on the container can be read by a bar code scanner when the container is in the holder.

16. A label system for ensuring proper positioning of bar code information on a label, comprising:

a first label comprising alignment symbology; and a second label comprising an alignment area corresponding to said alignment symbology of said first label such that said second label is positioned over said first label and the alignment area of the second label is aligned with the alignment symbology of the first label;

the second label further comprising demarcation indicia, positioned to align the container bearing the second label in a holder, so that information on the container can be read when the container is in the holder.

17. The label system of claim 16, further comprising visibility enhancement indicia adjacent the alignment area on the second label.

18. The label system of claim 16, wherein said alignment area is an opening in said second label.

19. The label system of claim 16, wherein said alignment symbology is a protrusion on said first label.

20. The label system of claim 16, wherein said alignment area is a transparent portion of said second label.

* * * * *